United States Patent
Bille

(10) Patent No.: US 7,703,923 B2
(45) Date of Patent: Apr. 27, 2010

(54) SYSTEM AND METHOD FOR IMAGING RETINAL TISSUE WITH TISSUE GENERATED LIGHT

(75) Inventor: Josef F. Bille, Heidelberg (DE)

(73) Assignee: Heidelberg Engineering GmbH, Heidelberg (DE)

( * ) Notice: Subject to any disclaimer, the term of this patent is extended or adjusted under 35 U.S.C. 154(b) by 40 days.

(21) Appl. No.: 12/205,309

(22) Filed: Sep. 5, 2008

(65) Prior Publication Data

US 2010/0060853 A1    Mar. 11, 2010

(51) Int. Cl.
A61B 3/10    (2006.01)
(52) U.S. Cl. .................. 351/221; 351/206; 351/246
(58) Field of Classification Search .................. 351/205, 351/206, 210, 221
See application file for complete search history.

(56) References Cited

U.S. PATENT DOCUMENTS

| 4,665,913 A | 5/1987 | L'Esperance, Jr. |
| 4,754,328 A | 6/1988 | Barath et al. |
| 4,781,453 A | 11/1988 | Kobayashi |
| 4,881,808 A | 11/1989 | Bille et al. |
| 5,772,298 A | 6/1998 | Miyake |
| 7,360,897 B2 * | 4/2008 | Kikuta et al. ............ 351/206 |
| 2004/0002694 A1 | 1/2004 | Pawlowski et al. |
| 2005/0159662 A1 | 7/2005 | Yoshikazu |

OTHER PUBLICATIONS

La Schiazza, Olivier et al., "High-Speed Two-Photon Autofluorescence Imaging of Human Retinal Pigment Epithelial Cells Toward Age-Related Macular Degeneration Diagnostic", University of Heidelberg, Heidelberg, Germany,(2008).
Agopov, M. et al., "SHG Imaging of the Pig Lamina Cribrosa Using a Novel Scanning Laser Ophthalmoscope-Based-Video-Rate Microscope", Kirchhoff- Institute for Physics, Heidelberg, Germany, (2008).
Biss, David, P., et al., "An adaptive optics biomicroscope for mouse retinal imaging," Proc. of SPIE, vol. 6467, 646703, (Feb. 6, 2007), XP007910922, p. 1-8.

* cited by examiner

Primary Examiner—Huy K Mai
(74) Attorney, Agent, or Firm—Nydegger & Associates

(57) ABSTRACT

A system and method for imaging retinal tissues in an eye generates an input light beam having ultra-short pulses and an input wavelength ($\lambda_i$) to stimulate the tissue. Depending on the particular type tissue being imaged, the retinal tissue responds to the input beam by generating a return beam of light having first and second components of different wavelengths ($\lambda_{r1}$ and $\lambda_{r2}$). An imaging unit then receives the return light and images the tissue according to the return wavelength ($\lambda_{r1}$ vis-a-vis $\lambda_{r2}$). Additionally, a sensor unit is used to evaluate light returning from the retina to measure optical and phase aberrations introduced by the eye, and to program a compensator (e.g. an active mirror) that compensates the input beam by removing the aberrations.

20 Claims, 2 Drawing Sheets

SYSTEM AND METHOD FOR IMAGING RETINAL TISSUE WITH TISSUE GENERATED LIGHT

FIELD OF THE INVENTION

The present invention pertains generally to ophthalmic diagnostic equipment. More particularly, the present invention pertains to systems and methods for imaging retinal tissue. The present invention is particularly, but not exclusively, useful as a system and method for stimulating tissue with a light beam of ultra-short pulses having an input wavelength that generates a return beam having different wavelength components depending on the type of retinal tissue being imaged.

BACKGROUND OF THE INVENTION

Effective imaging of the retina of an eye depends on the type of retinal tissue that is to be imaged, as well as the optical response of that tissue to the input light beam. In particular, for two specific tissues of the retina, namely the Retina Pigment Epithelium (RPE) and the Lamina Cribrosa (LC), it happens there are two different optical phenomena that generate the particular tissue's response. One is known as Two Photon Excited Fluorescence (TPEF). This phenomenon is efficacious for imaging the RPE of the retina. The other phenomenon is Second Harmonic Generation (SHG), which is efficacious for imaging the LC. An ability to image these tissues (i.e. RPE or LC) depends on how these phenomena are exploited.

Anatomically, RPE tissue in the retina includes the protein, lipofuscin. In the context of the present invention, it is known that lipofuscin is susceptible to TPEF. Specifically, it can be demonstrated that when an input beam of red light (e.g. $\lambda_i$=780 nm) is incident on lipofuscin in the RPE, a resultant return beam of fluorescent green light (e.g. $\lambda_{r1}$=530 nm) is generated. On the other hand, when this same input beam of red light ($\lambda_i$) is incident on the LC there is a much different response. Specifically, as a result of SHG, a return beam of blue light (e.g. % $\lambda_{r2}$=390 nm) is generated. (Note: $\lambda_i \neq \lambda_{r1} \neq \lambda_{r2}$). Nevertheless, both of the return beams ($\lambda_{r1}$ and $\lambda_{r2}$) are useable for effectively imaging the respective tissues.

During an imaging procedure, it happens that the anterior components of the eye (i.e. the cornea and the lens) will introduce optical aberrations into the input light beam. Also, the retina will introduce optical and phase aberrations. These aberrations, both optical and phase aberrations, are measurable. Furthermore, using adaptive optics with a wavefront sensor, the input light can be altered to effectively compensate for any optical aberrations that may be present. Further, phase aberrations that are introduced by curvature of the retina can be compensated for by pre-programming input to a computer that controls the adaptive optics.

In light of the above, it is an object of the present invention to provide a system and method that is capable of alternatively imaging the RPE or the LC tissues in a retina of an eye. Another object of the present invention is to provide a system and method that is capable of selectively exploiting the TPEF or SHG phenomenon to image different tissue in the retina of an eye. Yet another object of the present invention is to provide a system and method for imaging selective tissue in the retina of an eye that is easy to implement, is simple to use and is comparatively cost effective.

SUMMARY OF THE INVENTION

A system and method for imaging tissue in the retina of an eye includes a laser unit for generating an ultra-short pulsed input light beam having a wavelength ($\lambda_i$). As envisioned for the present invention, when the input light beam ($\lambda_i$) is incident on a target tissue, the tissue will generate a return light beam ($\lambda_r$). Importantly, this return light beam will include different wavelength components (i.e. $\lambda_{r1}$ and $\lambda_{r2}$) depending on the nature of the target tissue. In accordance with the present invention, this return light beam is then used for two different purposes. For one, regardless of wavelength, the return beam includes information that can be used to compensate for optical and phase aberrations that are introduced into the input beam by the eye. For another, depending on which component of the return beam is predominant (i.e. $\lambda_{r1}$ vis-a-vis $\lambda_{r2}$) the selected component can be used to image the particular retinal tissue that generates the return light beam.

Structurally, along with the laser unit that is used for generating the input light beam, the system for the present invention also includes a sensor with adaptive optics. For the present invention, the sensor has a wavefront sensor for measuring optical aberrations (e.g. a Hartmann Shack sensor) that is electronically connected with an active mirror. Together, the wavefront sensor and the active mirror are employed to alter the input light beam in a manner that will compensate for optical and phase aberrations introduced into the input beam. The system also includes a detector that receives the return light beam and uses it for imaging the target tissue that has been illuminated by the input beam.

For imaging purposes, the present invention directs the input light beam onto the target tissue that is to be imaged (e.g. RPE or LC). Preferably the input light beam is red light having a wavelength of about $\lambda_i$=780 nm. In the case of the RPE, because the target tissue includes lipofuscin, the tissue responds with TPEF by generating a return beam of green fluorescent light ($\lambda_{r1}$=580 nm). In the case of the LC, however, the target tissue responds with SHG by generating a return beam of blue light ($\lambda_{r2}$=390 nm). In each case, regardless of the type tissue being imaged, the return light is received by the detector for subsequent imaging of the tissue.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
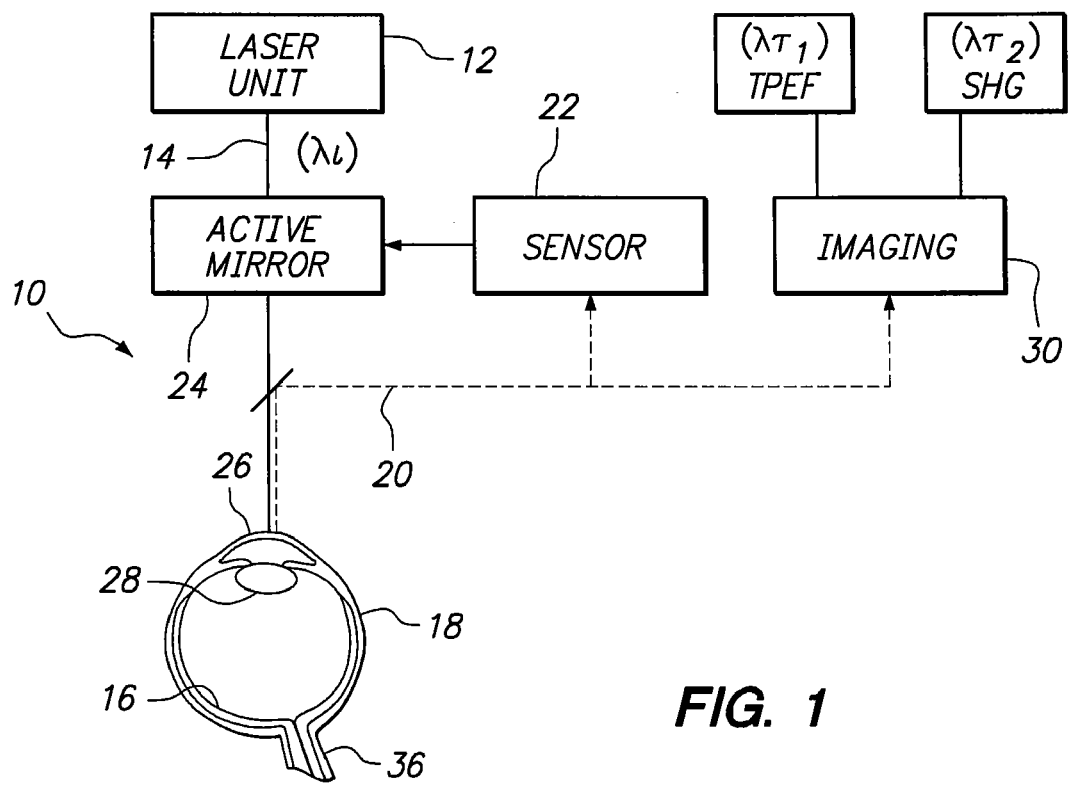
FIG. 1 is a schematic view of the components of a system for the present invention.

Referring initially to FIG. 1, a system in accordance with the present invention is shown and is generally designated 10. More specifically, as shown, the system 10 includes a laser unit 12 for generating an input laser beam 14. For the present invention, the input laser beam 14 is preferably a pulsed laser beam wherein the pulses are ultra-short and each pulse has a duration measured in femto-seconds. Further, the input laser beam 14 preferably has a wavelength ($\lambda_i$) that is about 780 nm ($\lambda_i$=780 nm). FIG. 1 also indicates that the input laser beam 14 is directed from the laser unit 12, and onto the retina 16 of an eye 18. As intended for the present invention, when the input light beam 14 ($\lambda_i$) is incident on tissue in the retina 16, it will interact with the tissue to generate a return light beam 20. Importantly, the return light beam 20 may include either, or both, of two different components that will have different wavelengths. Stated differently, the return light beam 20 will include a first component having a wavelength ($\lambda_{r1}$) and a second component with a wavelength ($\lambda_{r2}$). Note: $\lambda_i \neq \lambda_{r1} \neq \lambda_{r2}$.

Still referring to FIG. 1 it will be seen that, in addition to the laser unit 12, the system 10 includes a sensor unit 22 and an active mirror 24. Specifically, these elements of the system 10 (i.e. sensor unit 22 and active mirror 24) are used to pre-compensate the input beam 14 to create a diffraction limited spot on the retina 16. On this point it is well known that the cornea 26 and lens 28 of the eye 18 will introduce optical aberrations into the input light beam 14. Also, the retina 16 will introduce phase aberrations that continue with the return light beam 20. In order to measure the optical aberrations, the sensor unit 22 is preferably a wavefront sensor of a type well known in the pertinent art, such as a Hartmann Shack sensor. On the other hand, phase aberrations introduced by the retina 16 are preferably compensated for by pre-programming a computer to account for curvature of the retina 16. It is known, however, that some phase aberrations can be detected by fluorescence wavefront analysis. Therefore, the sensor unit 22 may also include this capability.

Once optical and phase aberrations in a return light beam 20 have been measured by the sensor unit 22, the aberrations can then be used to program an active mirror 24 (i.e. the computer used for operation of the active mirror 24). Specifically, the active mirror 24 is to be programmed in a manner that will change the input light beam 14 to thereby effectively remove the aberrations from the return light beam 20. Alternatively, a customized phase plate 29 (see FIG. 5) of a type disclosed in co-pending U.S. application Ser. No. 12/204,674 which is assigned to the same assignee as the present invention can be used with, or without, the active mirror 24 for this purpose. Importantly, the now-compensated return light beam 20 can be used by the imaging unit 30 for imaging purposes.

Figure 2:
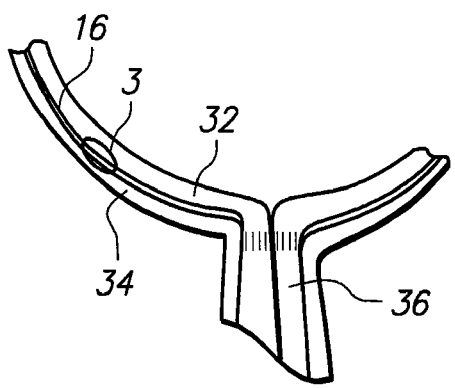
FIG. 2 is a cross sectional view of a portion of a retina of an eye.
Figure 3:
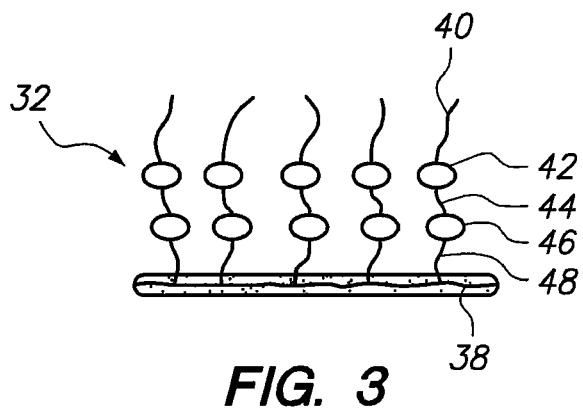
FIG. 3 is an enlarged view of retinal tissue (i.e. RPE) in the area bounded by the line 3-3 in FIG. 2.
Figure 4:
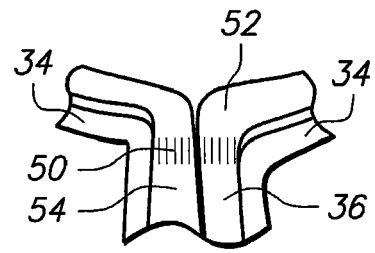
FIG. 4 is an enlarged view of retinal tissue (i.e. LC) in the optical nerve head.

Anatomically, an optic (visual) part 32 of the retina 16 comprises most of what is generally referred to as the fundus. As shown in FIG. 2, the sclera 34 is under the optic (visual) part 32, and the optical nerve head 36 connects to the optic (visual) part 32 through the sclera 34. In detail, with reference to FIG. 2 and FIG. 3 it will be seen that the optic (visual) part 32 of the retina 16 is curved and includes a Retina-Pigment-Epithelium (RPE) 38. The RPE 38 is a target tissue of interest for the present invention. Anterior to the RPE 38 and identified in an anterior to posterior direction, are: nerve fibers 40; retinal ganglion cells 42; axion 44; bipolar cell 46; and a photo receptor 48. Of these, as indicated above, it is the RPE 38 with its lipofuscins that responds to the input beam ($\lambda_i$) to generate a return beam ($\lambda_{r1}$) 20 due to TPEF. Referring now to FIG. 4, it will be seen that the optical nerve head 36 anatomically includes the Lamina Cribrosa (LC) 50 which is bounded by pre-laminar tissue 52 and post-laminar tissue 54. As also indicated above, the LC 50 is also a target tissue of interest for the present invention. In this case, the LC 50 responds to the input beam 14 ($\lambda_i$) to generate a return beam 20 ($\lambda_{r2}$) due to SHG.

Figure 5:
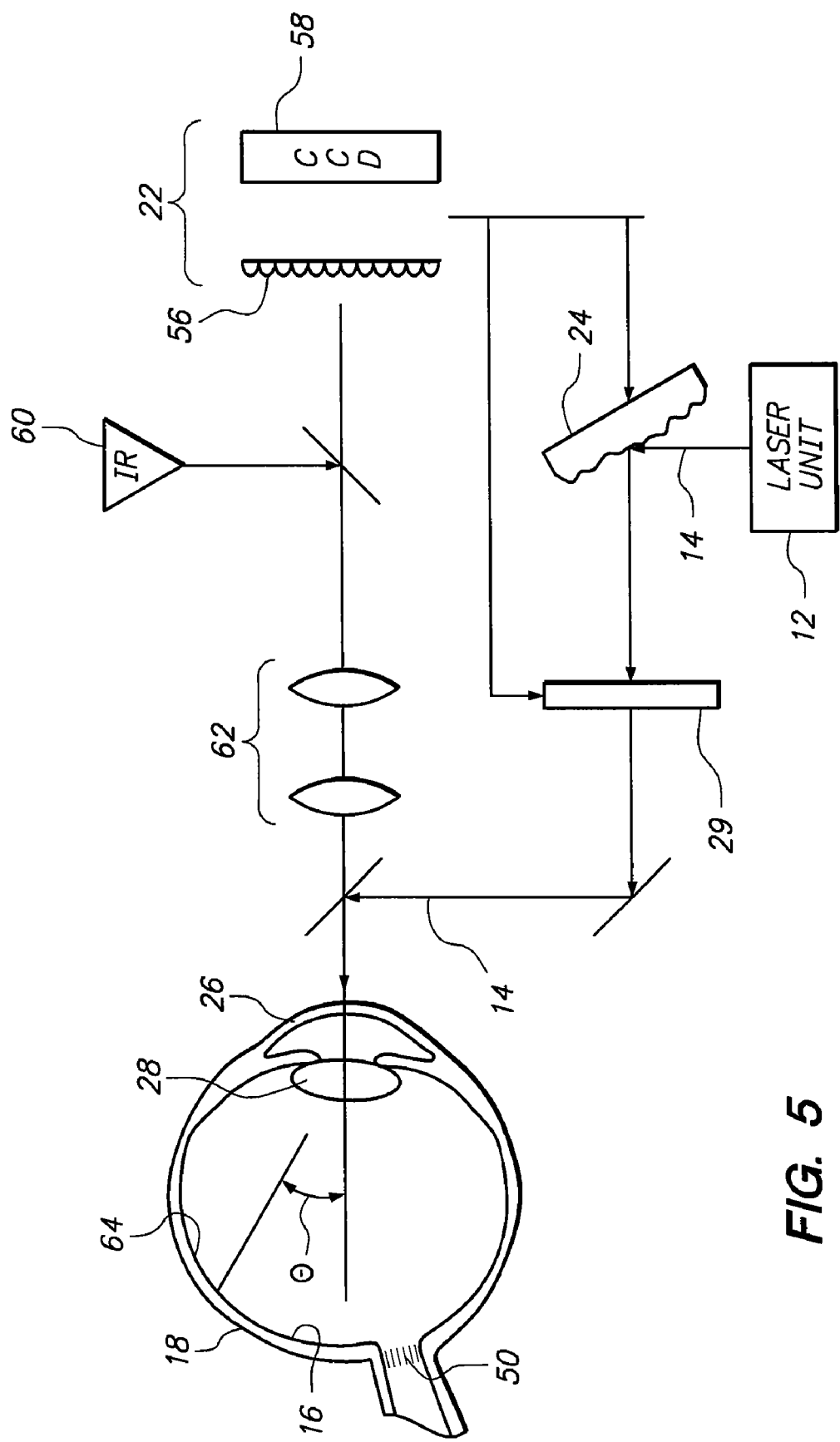
FIG. 5 is a schematic of the aberration compensation mechanism of the system.

Additional aspects of aberration compensation for the present invention can be appreciated with reference to FIG. 5. There the sensor unit 22 is shown to include a lens array 56, and a CCD camera 58. This arrangement is typical for a wavefront sensor of the type commonly referred to as a Hartmann-Shack sensor. FIG. 5 also indicates that a customized phase plate 29 can be used together with, or in lieu of, the active mirror 24. In either case, the importance of the arrangement is to compensate the input beam 14 for aberrations that could otherwise diminish the efficacy of the imaging system 10. Anatomically, there are three sources for these aberrations; all from the eye 18 itself. They are: 1] optical aberrations introduced by the anterior segment (i.e. cornea 26 and lens 28); 2] phase aberrations introduced by the curvature of the retina 16 that relate to astigmatism; and 3] phase aberrations introduced by the retina 16.

Of all the aberrations introduced by an eye 18 into the input light beam 14, optical aberrations are the most prominent, and are measured by the sensor unit 22. To do this, a source 60 of infrared (IR) light radiates IR through pupil imaging optics 62. Also, the Internal Limiting Membrane (ILM) 64 that defines the anterior surface of the retina 16 includes aberrational information in the light that is reflected from the retina 16. After leaving the eye 18, the optical aberrations that are introduced into the return beam 20 by the cornea 26 and lens 28 are processed by the sensor unit 22. The resultant information is then programmed into the active mirror 24. This essentially compensates for the first source of aberrations (i.e. the anterior segments). As for the second source of aberrations (i.e. phase aberrations introduced by the curvature of the retina 16) it is well known that these aberrations can be measured in accordance with the angle of incidence, "$\theta$", between the input light beam 14 and the anterior surface of the retina 16. Accordingly, "$\theta$" is determined by anatomical dimensions of the retina 16. The resultant measurements involving "$\theta$" are then also programmed into the computer-controlled active mirror 24. The remaining aberrations from the third source (i.e. the retina 16), although relatively minor, can be detected by a fluorescence wavefront sensor in the sensor unit 22 and used with the other information to further refine compensation corrections for the system 10.

As mentioned above, and as shown in FIG. 5, a custom phase plate 29 can be used in combination with the active mirror 24, or in lieu thereof. In either configuration, the purpose is to pre-compensate the input light beam 14 so that aberrations introduced into the light beam 14 do not detract from the imaging capability of the system 10.

While the particular System and Method for Imaging Retinal Tissue with Tissue Generated Light as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for imaging retinal tissues of an eye which comprises:
    a laser unit for generating an input beam having a wavelength $\lambda_i$, and for directing the input beam to a spot in the retina of an eye to generate a return beam from a retinal tissue, wherein the return beam has a first component with a wavelength $\lambda_{r1}$ and a second component with a wavelength $\lambda_{r2}$, wherein $\lambda_i \neq \lambda_{r1} \neq \lambda_{r2}$;
    a sensor unit for evaluating light returned from the retina to identify optical and phase aberrations introduced into the return beam by components of the eye;
    a compensator responsive to the sensor unit for altering the input beam to compensate the input beam by removing optical aberrations therefrom; and
    an imaging unit for receiving the return beam and imaging the retinal tissue by using a selected component in the return beam ($\lambda_{r1}$ vis-a-vis $\lambda_{r2}$).

2. A system as recited in claim 1 wherein the input beam includes a plurality of femto-second pulses and the wavelength of the input beam "$\lambda_i$" is 780 nm.

3. A system as recited in claim 2 wherein the first component of the return beam is generated by Two Photon Excited Fluorescence (TPEF) and the wavelength of the first component of the return beam "$\lambda_{r1}$" is approximately 530 nm.

4. A system as recited in claim 3 wherein the first component of the return beam is used by the imaging unit to image the Retina Pigment Epithelium (RPE).

5. A system as recited in claim 2 wherein the second component of the return beam is generated by Second Harmonic Generation (SHG) and the wavelength of the second component of the return beam "$\lambda_{r2}$" is approximately 390 nm.

6. A system as recited in claim 5 wherein the second component of the return beam is used by the imaging unit to image the Lamina Cribrosa (LC).

7. A system as recited in claim 1 wherein the compensator is an active mirror and the sensor unit comprises:
    an infrared (IR) wavefront sensor for measuring optical aberrations introduced by anterior elements of the eye; and
    a fluorescence wavefront sensor for measuring phase aberrations introduced by retinal tissue in the eye.

8. A system for imaging tissues of an eye which comprises:
    a laser means for directing an input beam onto a target tissue to be imaged, wherein the input beam includes a plurality of femto-second pulses having a wavelength "$\lambda_i$" and wherein the input beam generates a return beam from the target tissue having a first component with a wavelength "$\lambda_{r1}$" in response to a first target tissue, and a second component with a wavelength "$\lambda_{r2}$" in response to a second target tissue, and further wherein $\lambda_i \neq \lambda_{r1} \neq \lambda_{r2}$; and
    an imaging unit for selecting a component of the return beam ($\lambda_{r1}$ vis-a-vis $\lambda_{r2}$) for use in imaging the target tissue.

9. A system as recited in claim 8 further comprising:
    a sensor unit for evaluating light returned from the retina to identify optical and phase aberrations introduced into the return beam by components of the eye; and
    a compensator for altering the input beam to compensate the input beam by removing optical and phase aberrations identified by the sensor therefrom.

10. A system as recited in claim 9 wherein the compensator is an active mirror and the sensor unit comprises:
    an infrared (IR) wavefront sensor for measuring optical aberrations introduced by anterior elements of the eye; and
    a fluorescence wavefront sensor for measuring phase aberrations introduced by retinal tissue in the eye.

11. A system as recited in claim 8 wherein the wavelength of the input beam $\lambda_i$ is 780 nm.

12. A system as recited in claim 11 wherein the first component of the return beam is generated by Two Photon Excited Fluorescence (TPEF) and the wavelength of the first component of the return beam "$\lambda_{r1}$" is approximately 530 nm.

13. A system as recited in claim 12 wherein the first component of the return beam is used by the imaging unit to image the first retinal tissue, Retina Pigment Epithelium (RPE).

14. A system as recited in claim 8 wherein the second component of the return beam is generated by Second Harmonic Generation (SHG) and the wavelength of the second component of the return beam "$\lambda_{r2}$" is approximately 390 nm.

15. A system as recited in claim 14 wherein the second component of the return beam is used by the imaging unit to image the second target tissue Lamina Cribrosa (LC).

16. A method for imaging tissues in an eye which comprises the steps of:
    directing an input beam onto a target tissue to be imaged, wherein the input beam includes a plurality of femto-second pulses having a wavelength "$\lambda_i$" and wherein the input beam generates a return beam from the target tissue having a first component with a wavelength "$\lambda_{r1}$" in response to a first target tissue, and a second component with a wavelength "$\lambda_{r2}$" in response to a second target tissue, and further wherein $\lambda_i \neq \lambda_{r1} \neq \lambda_{r2}$; and
    selecting a component of the return beam ($\lambda_{r1}$ vis-a-vis $\lambda_{r2}$) for use in imaging the target tissue.

17. A method as recited in claim 16 wherein the wavelength of the input beam $\lambda_i$ is 780 nm, wherein the first component of the return beam is generated by Two Photon Excited Fluorescence (TPEF) and the wavelength of the first component of the return beam $\lambda_{r1}$ is approximately 530 nm, and further wherein the first component of the return beam is used by the imaging unit to image the first target tissue, Retina Pigment Epithelium (RPE).

18. A method as recited in claim 16 wherein the wavelength of the input beam $\lambda_i$ is 780 nm, wherein the second component of the return beam is generated by Second Harmonic Generation (SHG) and the wavelength of the second component of the return beam $\lambda_{r2}$ is approximately 390 nm, and further wherein the second component of the return beam is used by the imaging unit to image the second target tissue, Lamina Cribrosa (LC).

19. A method as recited in claim 16 further comprising the steps of:
    evaluating light returned from the retina to identify optical and phase aberrations introduced into the return beam by components of the eye; and
    altering the input beam to compensate the input beam by removing optical and phase aberrations therefrom.

20. A method as recited in claim 19 wherein the evaluating step is accomplished using an infrared (IR) wavefront sensor for measuring optical aberrations introduced into the input beam by anterior elements of the eye, and using a fluorescence wavefront sensor for measuring phase aberrations introduced into the input beam by retinal tissue.

* * * * *